United States Patent [19]

Todd et al.

[11] Patent Number: 5,708,197
[45] Date of Patent: Jan. 13, 1998

[54] HELICAL BARREL RHEOMETER

[75] Inventors: David B. Todd, Princeton; Costas G. Gogos, Wyckoff; Demosthenis Chaparampopoulos, North Bergen, all of N.J.

[73] Assignee: Polymer Processing Institute, Hoboken, N.J.

[21] Appl. No.: 643,881

[22] Filed: May 7, 1996

[51] Int. Cl.⁶ ................................................. G01N 11/14
[52] U.S. Cl. ........................................ 73/54.28; 73/54.35
[58] Field of Search ............................. 73/54.04, 54.09, 73/54.11, 54.14, 54.23, 54.28, 54.35

[56] References Cited

U.S. PATENT DOCUMENTS

| | | | |
|---|---|---|---|
| 1,810,992 | 6/1931 | Von Dallwitz-Wegner | 73/54.04 X |
| 1,848,928 | 3/1932 | Bechstrom et al. | 72/54.14 |
| 4,448,736 | 5/1984 | Emery et al. | 264/40.1 |
| 4,468,953 | 9/1984 | Garritano | 73/54.39 |
| 4,501,155 | 2/1985 | Garritano | 73/847 |
| 4,541,270 | 9/1985 | Hanslik | 73/54.11 |
| 4,601,195 | 7/1986 | Garritano | 73/54.34 |
| 4,627,272 | 12/1986 | Wright | 73/54.23 |
| 4,817,416 | 4/1989 | Blanch et al. | 73/54.04 |
| 4,864,849 | 9/1989 | Wright | 73/54.31 |
| 4,878,378 | 11/1989 | Harada | 73/54.35 |
| 4,934,201 | 6/1990 | Grimminger et al. | 73/864.81 |
| 5,115,669 | 5/1992 | Fuller et al. | 73/54.39 |
| 5,172,585 | 12/1992 | Gleissle | 73/54.04 |
| 5,205,158 | 4/1993 | Janulis | 73/54.06 |
| 5,209,108 | 5/1993 | Shackelford | 73/54.28 |
| 5,245,861 | 9/1993 | Limper et al. | 73/54.34 |
| 5,271,266 | 12/1993 | Eschbach | 73/54.33 |
| 5,315,863 | 5/1994 | Cowper | 73/54.09 |
| 5,347,852 | 9/1994 | Mode | 73/54.04 |
| 5,357,783 | 10/1994 | Eschbach | 73/54.33 |
| 5,456,105 | 10/1995 | James | 73/54.01 |

OTHER PUBLICATIONS

A. Gottfert, New Concept for on-line rheometry in real time, *Kunststoffe*, 81:1 (1991).

V. Morrow & J.F. Reilly, Improving correlation between on-line and lab rheology, *Plastics Engineering*, Sep., 1995, pp. 27–29.

R.D. Laversuchh & J. Myers, Role of resin consistency grows in quality control, *Modern Plastics*, Nov., 1993, pp. 46–50.

J. Garza & D. Glazner, A fast and easy way to measure viscosity, *Chemical Engineering*, Jun., 1995, p. 133.

P.W. Springer, R.S. Brodkey & R.E. Lynn, Development of an extrusion rheometer suitable for on–line rheological measurements, *Polymer Engineering and Science*, Aug., 1975, vol. 15, No. 8, pp. 583–587.

Low–shear–rate rheometry and polymer quality control, *Chem. Eng. Common*, 1985, vol. 32, pp. 1–60.

G.R. Zeichner & C.W. Macosko, On–Line viscoelastic measurements for polymer melt processes, IUPAC, International Union of Pure and Applied Chemistry, 28th Macromoleclar Symposium, paper presented at U. of Mass., Amherst, MA, Jul. 12–16, 1982 meeting, p. 861.

A Dreiblatt; H. Herrmann & H.–J. Nettelnbreker, On–line quality control for improved compounding, *Plastics Engineering*, Oct., 1987, pp. 31–34.

*Primary Examiner*—Michael Brock
*Attorney, Agent, or Firm*—Klauber & Jackson

[57] ABSTRACT

A rheometer and method for determining rheological characteristics of a composition, the rheometer including: a housing member; a helical flange disposed on an inner surface of the housing member; a rotor disposed concentrically within the helical flange and abutting the helical flange while maintaining sliding contact with the flange, wherein the rotor and the helical flange form a helical channel; a mechanism for rotating the rotor; a mechanism for introducing a sample of the composition into one end of the channel; a mechanism for controlling removal of the sample from the other end of the channel; and a mechanism for measuring a pressure difference of the sample between an upstream location and a downstream location in the channel.

14 Claims, 7 Drawing Sheets

HELICAL BARREL RHEOMETER

FIELD OF THE INVENTION

The present invention relates generally to an apparatus and process for the measurement of rheological properties of a composition and pertains, more specifically, to a helical barrel rheometer which facilitates such measurements over relatively wide ranges of temperature, pressure and shear rates for a wide variety of compositions. The rheometer may be used on-line with a process, or off-line, e.g. in the laboratory.

BACKGROUND OF THE INVENTION

Statistical process control and statistical quality control methods require the continuous on-line measurement of process variables. After identifying the process variables which affect quality, the process must be monitored and adjusted to minimize disturbances. One important process variable is often the viscosity of the composition being manipulated or produced. Also, the shear rate is an indication of the degree of mixing and the shear stress is an indication of the intensity of mixing. Various devices are known which may be used to make measurements of viscosity and elasticity of fluids such as polymer melts. These include capillary or slit flow devices, and devices which measure rheological quantities by determining the shear characteristics of the polymer melt.

Although viscosity measurements can be made in the laboratory, typically laboratory rheometers are not able to effectively and timely measure viscosity in the context of providing meaningful feedback for process control. Laboratory tests are also usually costly and cumbersome, and only periodic samples of a process can be tested.

As a result, various types of rheometers have been developed for on-line and in-line rheological testing of processes. On-line response may be approximately 1 to 2 minutes, while laboratory tests results may not be available for up to 4 hours in a typical lab test, although many on-line instruments also suffer long sampling and residence times. In extrusion processes, on-line rheology tests typically utilize a bypass extruder and a narrow capillary slit-die to measure a portion of the melt stream diverted from the main flow. For in-line rheology testing, a device for measuring flow properties is placed directly inside the extrusion system. Frequently, however, agreement between laboratory and on-line measurements of viscosity has not been satisfactory.

On-line rheometers sometimes use metering pumps and pressure transducers to generate and measure shear conditions. Typical on-line rheometers rely on process pressure to force a composition such as a polymer melt into a metering pump, which then generates the flow rate and pressure to extrude the composition polymer through a precision capillary or orifice. Orifice pressure is measured by one or more pressure transducers. Two of the most common on-line rheometers may be referred to as the "bypass" type and the "return stream" type.

In the bypass rheometer the sample exits to the atmosphere and often falls to the floor. A single pressure transducer is located above the capillary. This simple type of on-line rheometer very closely approximates the internal geometry of the ASTM plastometer and, therefore, the capillary entrance effects. A constant pressure at the inlet, as defined by the ASTM method, is set by controlling the metering pump flow rate. Typically a rated volumetric flow rate and a flow density yield mass flow rate and melt flow index (MFI) as a function of pump speed.

SUMMARY OF THE INVENTION

The present invention provides a rheometer for determining rheological characteristics of a composition. The rheometer comprises: a housing member; a helical flange disposed on an inner surface of the housing member; a rotor disposed concentrically within the helical flange and abutting the helical flange while maintaining sliding contact with the flange, wherein the rotor and the helical flange form a helical channel; a means for rotating the rotor; a means for introducing a sample of the composition into one end of the channel; a means for controlling removal of the sample from the other end of the channel; and a means for measuring a pressure difference of the sample between an upstream location and a downstream location in the channel. The pressure difference is measured while the rotor is rotating and removal of the sample from the helical channel is temporarily stopped.

The rheometer may further include a means for measuring the temperature of the sample at a point adjacent to at least one of the locations, and may even further comprise a means for controlling a temperature of the sample.

The upstream location and the downstream location of pressure measurement are preferably situated at least one flight apart within the helical channel.

The rheometer has the capability of allowing the sample to be continuously transported through the channel before and after the pressure difference measurement.

The rheometer has the capability of measuring the rheological properties of a wide variety of compositions under various conditions, either on-line or in the laboratory. For example, the composition measured may be a non-Newtonian fluid, such as a molten polymer, a polymer solution, a non-plastic material, a slurry, or a liquid with suspended coarse particles or dissolved gas. By way of further example, the rheometer may accommodate such materials as peanut butter, ice cream, or bread dough. The sample tested by the rheometer may be present in a molten form within the helical channel where the sample comprises a slipstream of a molten composition.

BRIEF DESCRIPTION OF THE DRAWINGS

Understanding of the present invention and the various aspects thereof will be facilitated by reference to the accompanying drawings.

DETAILED DESCRIPTION OF THE PREFERRED EMBODIMENTS

Reference is now be made to the drawings, on which similar or identical elements are given consistent identifying numerals throughout the various figures thereof, and on which parenthetical references to figure numbers direct the reader to the view(s) on which the element(s) being described is (are) best seen, although the element(s) may also be seen on other views.

In-line devices have been used in the process industry to follow morphology and viscosity changes in process flows brought about by various mixing configurations in single and twin-screw extruders. The in-line devices were "screw" extensions of a smooth cylinder rotating in a helically grooved barrel. In the metering section of a conventional extruder, the viscous flow rate, Q, is generally characterized in terms of a drag flow, $Q_d$, and a pressure flow, $Q_p$, as follows:

$$Q = Q_d - Q_p \quad (1)$$

where $$Q_d = F_d \pi D W h \cos(\Theta) N/2 \quad (2)$$

and $$Q_p = F_p W h^3 \Delta P \sin(\Theta) / \mu L / 12 \quad (3)$$

where:
h=depth of the helical channel
W=width of the helical channel
D=mean diameter of the helical flight
L=axial length of the extruder
N=rotational speed of rotor p1 μ=viscosity of composition
Θ=helical angle of flight $F_d$ and $F_p$ are shape correction factors.

At a closed discharge, i.e. for closed Couette flow, the drag flow and pressure flow are equal, and the pressure developed can be used as a measure of apparent viscosity. With a shallow channel, the pressure drop across k flights, $\Delta P_k$, is as follows:

$$\Delta P_k = 6k\pi^2 N\mu D^2/h^2 \quad (4)$$

where k is the number of flights, and therefore $$\mu = \Delta P_k h^2/(6\pi^2 N\eta D^2 k) \quad (5)$$

Thus, viscosity can be easily determined by measurement of pressure drop across a single flight, or integral number of flights, without measurement of flow rate or torque. As related to the screw-type metering section, however, the pressure fluctuations, which occur due to the passage of flight tips past the pressure taps, make accurate pressure measurement difficult.

Figure 1:
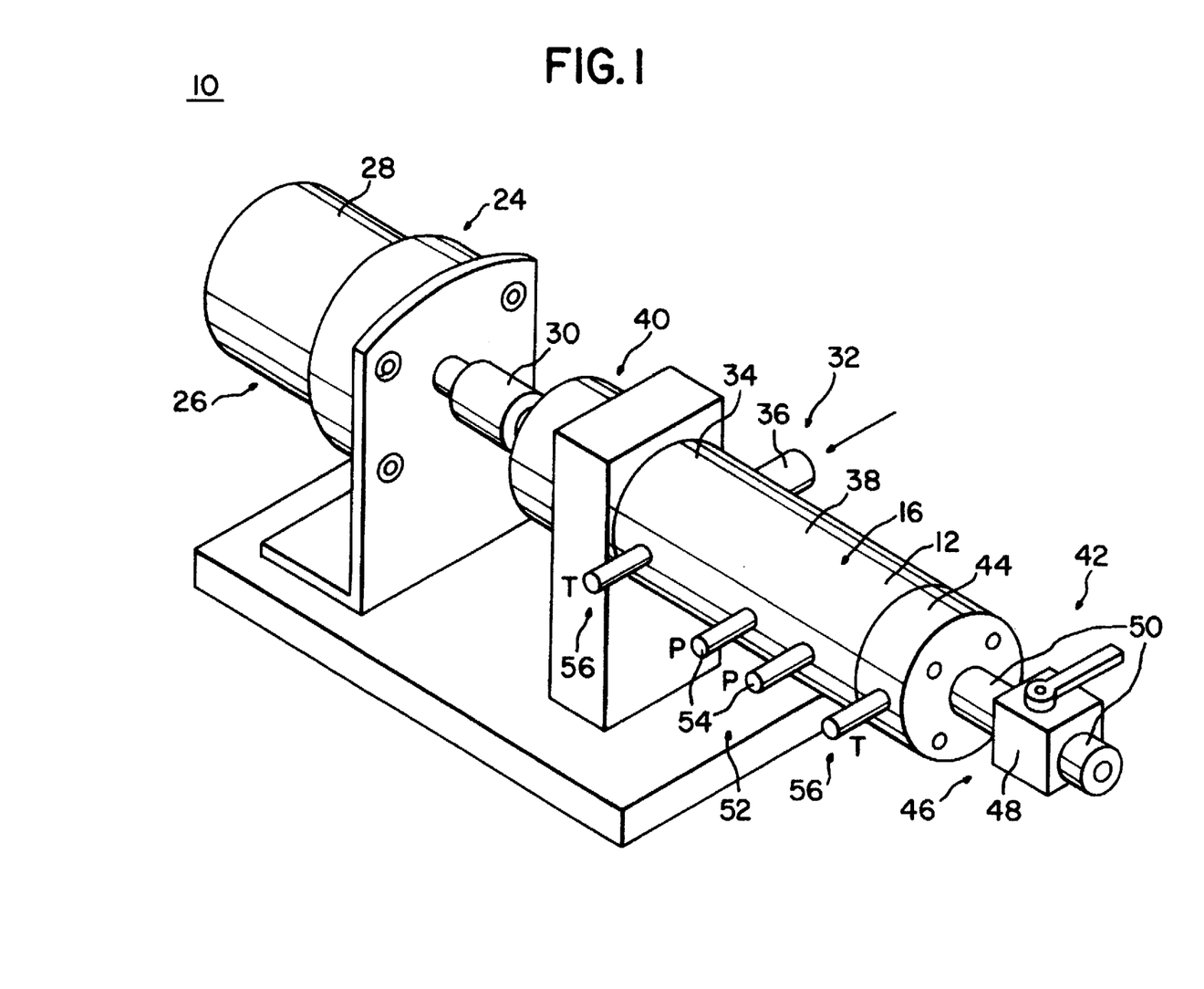
FIG. 1 is a perspective view of an embodiment of the helical barrel rheometer of the invention.
Figure 2:
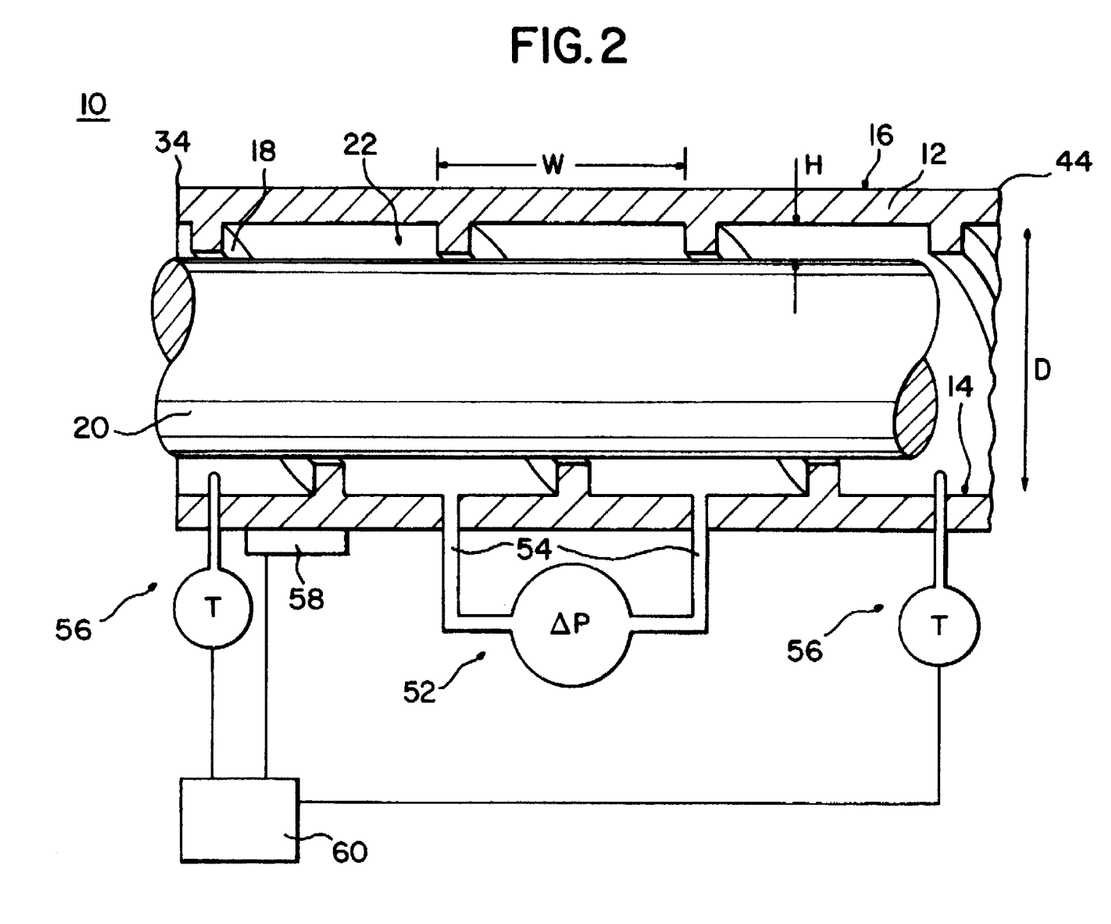
FIG. 2 is a side cutaway view of a portion of the helical barrel rheometer of FIG. 1.

The present invention solves this problem by taking the opposite approach to the well-known rotating screw-type extruder which has a helical screw blade that rotates inside a cylindrical housing. Instead, the present invention provides a helical barrel rheometer 10 which is preferably an extruder-like device in which a helical channel 22 is provided on the inner surface 14 of a stationary housing member 12 and a concentric cylindrical rotor 20 disposed inside the housing member which rotates to impart motion to a material introduced into the housing member, as illustrated in FIGS. 1 and 2. The helical barrel rheometer 10 can be readily portable and can operate as a stand-alone unit.

In the context of on-line operation, a slip stream of a composition such as a polymer melt is fed from the process extruder (or reactor) to the inlet side of the rheometer. As the composition fills the helical channel, the rheometer develops pressure inside the helical channel by transporting the composition to one end by drag forces. After leaving the rheometer, the slip stream can be directed to circulate through some other type of detection cell, such as for near infrared or Fourier transform infrared analysis, and possibly returned to the process.

Both pressure drop and inlet and exit temperatures may be measured and recorded while the exit valve is closed and the rotor continues to rotate, and measurements can be made over a range of rotor speeds.

For Newtonian flow, the viscosity μ is the proportionality between shear stress σ and shear rate $\dot{\gamma}$:

$$\mu = \sigma/\dot{\gamma} \quad (6)$$

For some viscous liquids, the viscosity is not independent of shear rate. For many such non-Newtonian liquids, the viscosity has been shown to be represented over the range of shear rates of interest by:

$$\mu = \sigma/\dot{\gamma}^n \quad (7)$$

Such liquids are called "power law" fluids.

The variation of viscosity with rotor speed, as determined from Equation (5), can be used to determine the power exponent n, by noting the slope of a log-log graph of viscosity versus rotor speed. The slope is (n−1).

The flow in the helical barrel rheometer at closed discharge is described as closed Couette flow. It has been determined that the equivalent shear rate $\dot{\gamma}_w$ for power law fluids in the helical barrel rheometer is:

$$\dot{\gamma}_w = (2+2/n)(\pi D N/h) \quad (8)$$

The term (2+2/n) for closed Couette flow is analogous to the Rabinowitsch correction factor for capillary flow.

The helical barrel rheometer of the invention has the capability of handling many types of composition under various conditions which cannot appropriately be measured in capillary or slit rheometers. For example, the viscosity of a polymer solution which is above its boiling point can be readily accommodated in the helical barrel rheometer because pressure is developed, rather than dissipated, inside the rheometer. By way of another example, fibrous material can be processed without difficulty.

It should also be noted that the viscosities of compositions as determined by the helical barrel rheometer of the invention may additionally be more representative of the effective viscosity of the composition occurring within the processing equipment, as well as being closer to laboratory rheometer test results under the same conditions, as seen below.

An embodiment of the rheometer 10 of the invention is illustrated in FIGS. 1 and 2. The rheometer 10 includes a housing member 12 having an inner surface 14 and an outer surface 16. The housing member shown in FIGS. 1 and 2 is cylindrically shaped about a longitudinal axis. A helical flange 18 is disposed on the inner surface 14 of the housing member 12. A rotor 20 is disposed concentrically within the helical flange 18 such that the rotor 20 abuts the helical flange 18 while maintaining sliding contact with the flange 18. Together the helical flange 18, the rotor 20, and at least a portion of the inner surface 14 define a helical channel 22 within the housing member 12 through which a composition may be transported. The rotor 20 is sized to abut the helical flange 18 snugly enough to substantially prevent the transport of a composition between the helical flange 18 and the rotor 20 in a generally longitudinal direction, which may be referred to as cross-leakage. Moreover, the rotor 20 is also sized to abut the helical flange 18 so that the rotor may be rotated without excessive torque demands. Thus, rotor 20 has a clearance relative to the flange 18 sufficient to ensure that a composition does not pass between rotor and the flange but at the same time does not introduce significant shear forces on the flange to retard its rotational motion.

It should be noted that a minimal amount of cross-leakage of the composition, although not preferable, may be tolerated during operation depending upon the composition and testing conditions. A thin layer of composition may occupy the narrow gap, if any gap exists, between the helical flange 18 and rotor 20, and the thin layer may provide lubrication between the flange and the rotor, while the helical channel 22 provides a transport path for the bulk of the composition occupying the housing member 12. On the other hand, the flange 18 and the rotor 20 may be fitted closely enough such that no appreciable gap exists.

A means 24 for rotating the rotor 20 is provided, shown in FIG. 2 as a motor assembly 26 including a motor 28 and shaft 30. A single speed motor may be used, although a variable speed motor would typically be used for making measurements at various speeds, i.e. to measure viscosity at various shear rates. The motor assembly 26 may further include a speed control means, not shown in the Figures, as is well known in the art. The means 24 for rotating the rotor 20 preferably includes a bearing means 40, which further preferably comprises a journal bearing and a thrust bearing encased in a bearing housing.

A means 32 for introducing a sample of the composition into one end of the helical channel 22 may be provided at one end 34 of the housing member 12, and includes an inlet port 36 which is capable of introducing the composition into the helical channel 22. The inlet port is shown in FIG. 1 as extending substantially perpendicularly through the housing member 12 on the cylindrical wall portion 38. It should be noted that the inlet port 36 may instead extend through the housing member 12 at another angle of the housing member and thus communicate with the helical channel 22.

A means 42 for controlling removal of the sample from the other end of the channel 22 is provided as shown in FIG. 1 as an exit assembly 46 which includes an exit valve 48 and an exit port 50. The exit value 48 may be a ball-valve or some other valve which can provide on/off operation. The exit valve 48 may be automatically controlled or manually operated. The exit port 50 is shown in FIG. 1 as extending substantially perpendicularly through the housing member 12 at the other end 44 of the housing member 12, such that a sample of composition may exit the rheometer 10 in an axial direction. It should be noted that the exit assembly 46 may instead be oriented so that the exit port 50 extends through the cylindrical wall portion 38 of the housing member 12. In any case, the exit assembly 46 communicates with the helical channel 22 at least one helical flight away from the location where the inlet port communicates with the channel.

In operation, the direction of rotation of the rotor 20 is selected to coincide and cooperate with the orientation of the helical channel 22. For example, FIG. 2 illustrates a helical flange 18 which, when viewed from the right end 44, spirals counterclockwise and inward. With that orientation of the helical flange 18, and with the composition entering from the left end 34 of the housing member 12 and exiting at the right end 44, the rotor 20 should be rotated in the clockwise direction when viewed from the right end 44.

Conversely, if the helical flange 18 spirals clockwise and inward, when viewed from the right end 44, and with the composition entering from the left end 34 of the housing member 12 and exiting at the right end 44, the rotor 20 should be rotated in the counterclockwise direction when viewed from the right end 44.

Thus, for example, a sample of the composition which is to be tested can be introduced into the helical chamber 22 through the inlet port 36 at the left end 34 of the housing member 12 as shown in FIGS. 1 and 2. The helical flange 18, when viewed from the right end 44, spirals counterclockwise and inward. As the rotor 20 is rotated in the clockwise direction when viewed from the right end 44, a portion of the sample inside the helical chamber 22 viscously adheres to the rotating rotor 20 and is dragged by the rotor, and the sample generally follows the rotational path of the rotor 20 and the axial spiral of the helical channel 22. The rotor 20 thus imparts a helical translation motion to the sample and thereby propels the sample from the inlet port 36, through the channel 22 toward the exit port 50. If the exit valve 48 is open, the sample is propelled out through the exit port 50. It should be understood that if the rotor 20 were rotated in the opposite direction, i.e. counterclockwise when viewed from the right end 44, the sample would be urged to travel in the "backward" direction, i.e., from the exit port 50 to the inlet port 36 configured as shown.

In on-line applications, the sample may be introduced into the rheometer 10 through the existing process pressure. The sample may additionally be passed through a gear pump prior to entry into the rheometer.

The sample which exits the rheometer may be recycled or reintroduced into a process flow, or directed elsewhere to be further processed or discarded.

In process applications, the rheometer 10 is preferably placed as close as possible to the process in order to minimize problems with control such as: lag time in reading the sample, pressure drop in the sample line, or sample temperature changing from the process temperature. The compact design afforded by the present invention, as illustrated by the embodiment in FIGS. 1 and 2, permits the rheometer 10 to be located directly alongside a process apparatus.

The rheometer 10 also includes a means 52 for measuring a pressure difference of the sample between an upstream location and a downstream location in the channel 22. The pressure difference may be measured by two pressure transducers mounted in, or on, pressure ports 54 extending through the housing member 12, one upstream from the other, and adapted to measure the normal pressure at the inner surface 14 of the housing member 12. As seen in FIG. 2, the pressure difference may be measured by a pressure difference sensor having a pair of pressure taps 54 mounted through the housing member 12, one upstream of the other. The pressure transducers and/or taps are preferably flush mounted with the housing inner surface 14, although some portion of the pressure transducer or tap 54 could extend into the helical channel 22. The pressure transducers or taps 54 are also preferably mounted at least one helical flight apart.

The rheometer 10 may also include a means 56 for measuring temperature of the sample at a point adjacent to at least one of the locations where pressure is measured in order to monitor the temperature of the sample inside the helical channel 22. The temperature measuring means 56 may include one or more temperature sensors which are mounted through the housing member. The temperature sensors may be flush mounted with the housing inner surface 14 or preferably some portion of the temperature sensor extends into the helical channel 22. It should be noted that, unlike rotating screw-type extruders and the like, the present invention permits the extension of the temperature (or other) sensor into the helical channel 22 thereby placing the sensor in contact with the composition and minimizing measurement errors due to end effects, etc.

The rheometer 10 may also further comprise a means for controlling a temperature of the sample, the temperature controlling means including the temperature sensors mentioned above or additional temperature sensors, a heating or cooling means 58, and a control means 60, as seen in FIG. 2.

In process applications, the temperature of the sample may vary from the process temperature due to many factors, such as the nature of the composition, its viscosity, thermal conductivity, and molecular weight; the volumetric flow rate of the sample; the rotor speed; the process pressure; the dimensions of the helical channel 22, the inlet port 36, and the exit port 50; the distance the sample must travel between the process and the rheometer 10; and environmental conditions such as air drafts, heat sources, and heat sinks. Although the present invention without a temperature control means could minimize these effects to the extent that active control of the sample temperature becomes unnecessary, the rheometer 10 could be provided with a temperature control means to compensate for undesirable temperature disturbances which are otherwise unavoidable.

Thus, in the operation of one embodiment of the present invention, a sample of a composition is fed into the inlet port 36 of the rheometer 10, either by a process pressure, a gravity feed, a metering pump, or some other motive means, while simultaneously the rotor 20 is rotated by the motor assembly 26 at a selected speed. The sample is transported generally along the helical path within the helical chamber 22 as a result of the viscous drag forces imparted to the sample by the rotating rotor 20. In addition, the sample may also be transported along the helical path by the pressure differential between the inlet port 36 and the exit port 50. The temperature of the sample may be monitored, and further may be controlled to a selected temperature. After a sufficient time has elapsed, or after the pressure difference $\Delta P_k$ has substantially approached a steady state value, the rheometer 10 is ready to measure a rheological property such as viscosity. Subsequently, a measurement is made while the rotor 20 continues to rotate, the exit valve 48 is temporarily closed, and the pressure difference between two points in the helical channel are measured. The exit valve 48 is preferably closed only for a relatively short time, usually less than one minute in the experiments described below, while the pressure measurement is made, and thereafter the exit valve 48 is opened to allow the sample to continue to exit the rheometer 10. Thus, the sample may continuously flow through the rheometer 10, interrupted only momentarily whenever a pressure measurement is made.

The rheometer 10 may be connected on-line to a process flow such that a side stream is diverted from the process flow and into the rheometer. Thus the rheometer 10 would be available to continuously monitor the rheological properties of the process flow.

A single batch, or batch sample, may be fed into the rheometer for a determination of its rheological properties. The batch sample preferably is large enough to fill the helical chamber completely or enough to at least ensure that the helical channel between the two pressure measurement points is substantially filled with the sample material.

The rheometer 10 of the invention may measure the rheological properties of many different types of composition, which includes, but is in no way limited to, polymer melt flows. The invention is compatible with a composition which may be a viscous fluid, either Newtonian or non-Newtonian. The composition may be a non-plastic material, which may include but is not limited to selection from a group of non-plastic materials such as peanut butter, ice cream, and bread dough. The sample may be present in a molten form within the helical channel, especially when the sample comprises a slipstream of a molten composition such as a polymer.

Thus, according to the invention, one method of measuring rheological properties of a composition would comprise the following steps: (a) placing the composition in contact with a rotating surface, such as the rotor 20; (b) dragging the composition in contact with the rotating surface along an enclosed helical path, such as helical path 22, thereby transporting the composition simultaneously in a rotational and an axial direction; and (c) restraining the transport of the composition in the axial direction while simultaneously measuring a pressure difference between an upstream and a downstream location in the helical path.

EXPERIMENTAL RESULTS

As discussed below, two rheometers, Rheometers I and II, were tested having dimensions as listed in Table 1.

TABLE 1

Experimental Helical Barrel Rheometer Parameters

| | HBR-I | HBR-II |
|---|---|---|
| Mean Diameter of Helical Flight, D (mm)* | 34.8 | 24.0 |
| Depth of Helical Channel, H (mm)* | 1.5 | 2.0 |

*cf. FIG. 2

Figure 3:
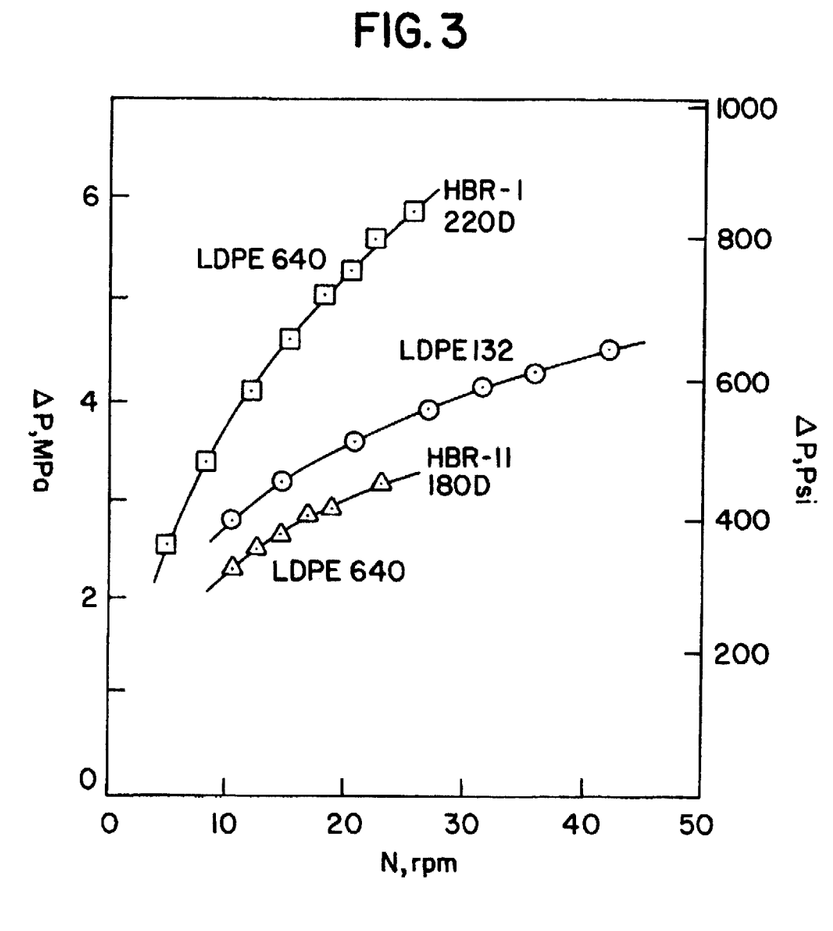
FIG. 3 shows experimental results of pressure difference at various rotor speeds for first and second embodiments of the helical barrel rheometer of the invention.

Experimental pressure difference measurements are shown plotted against various rotor speeds for two low density polyethylene ("LDPE") compositions in FIG. 3.

Figure 4:
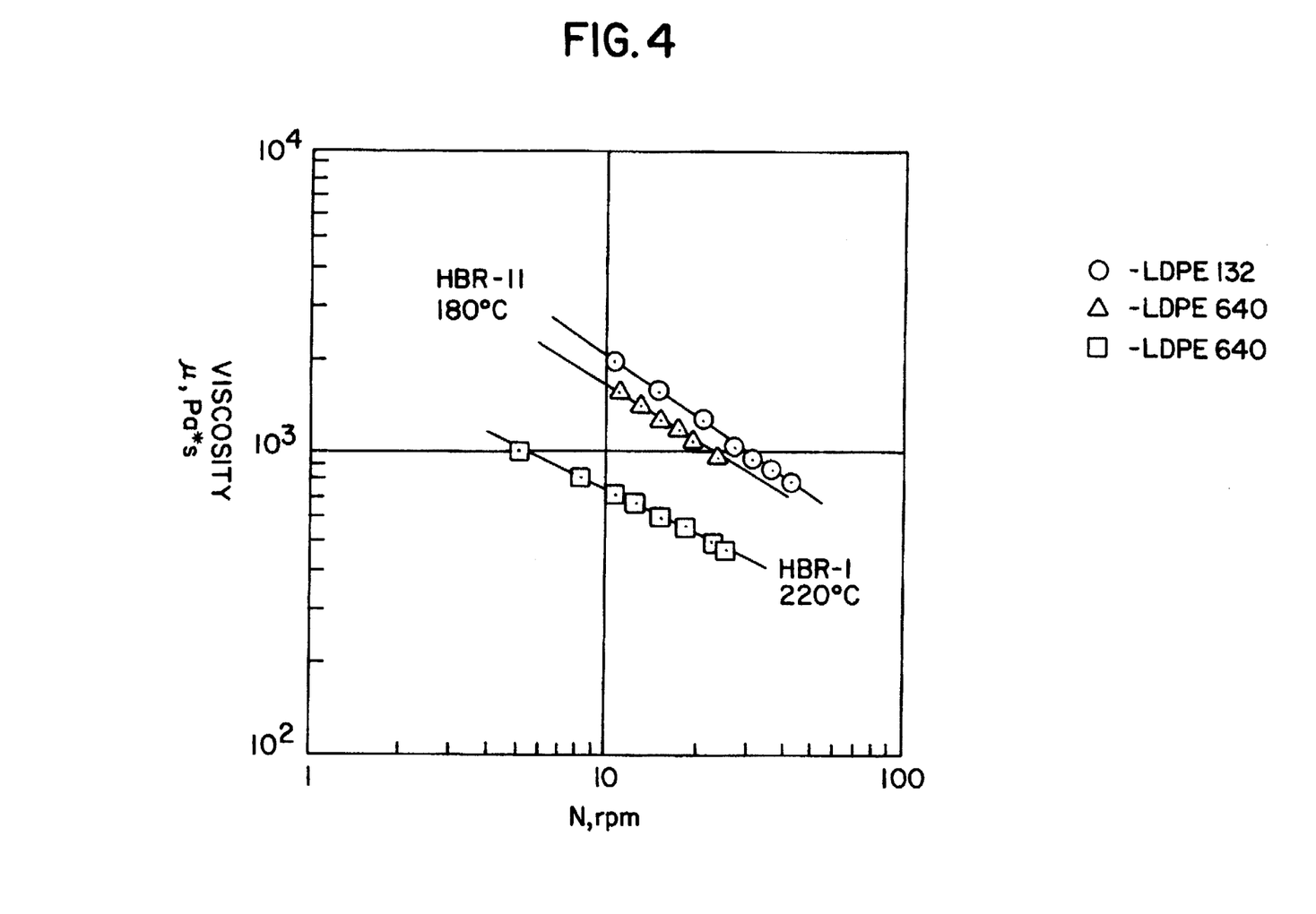
FIG. 4 shows experimental results of viscosity $\mu$, versus rotor speed, N, for three different compositions obtained in first and second embodiments of the helical barrel rheometer of the invention.

Experimental results of viscosity, $\mu$, versus rotor speed, N, for three different compositions are shown in FIG. 4. The slope of the plot of log $\mu$ versus log N is substantially equal to the quantity n−1. Thus, shear rates can be readily calculated from Equation 8 given the values for n, D, h, and N.

Figure 5:
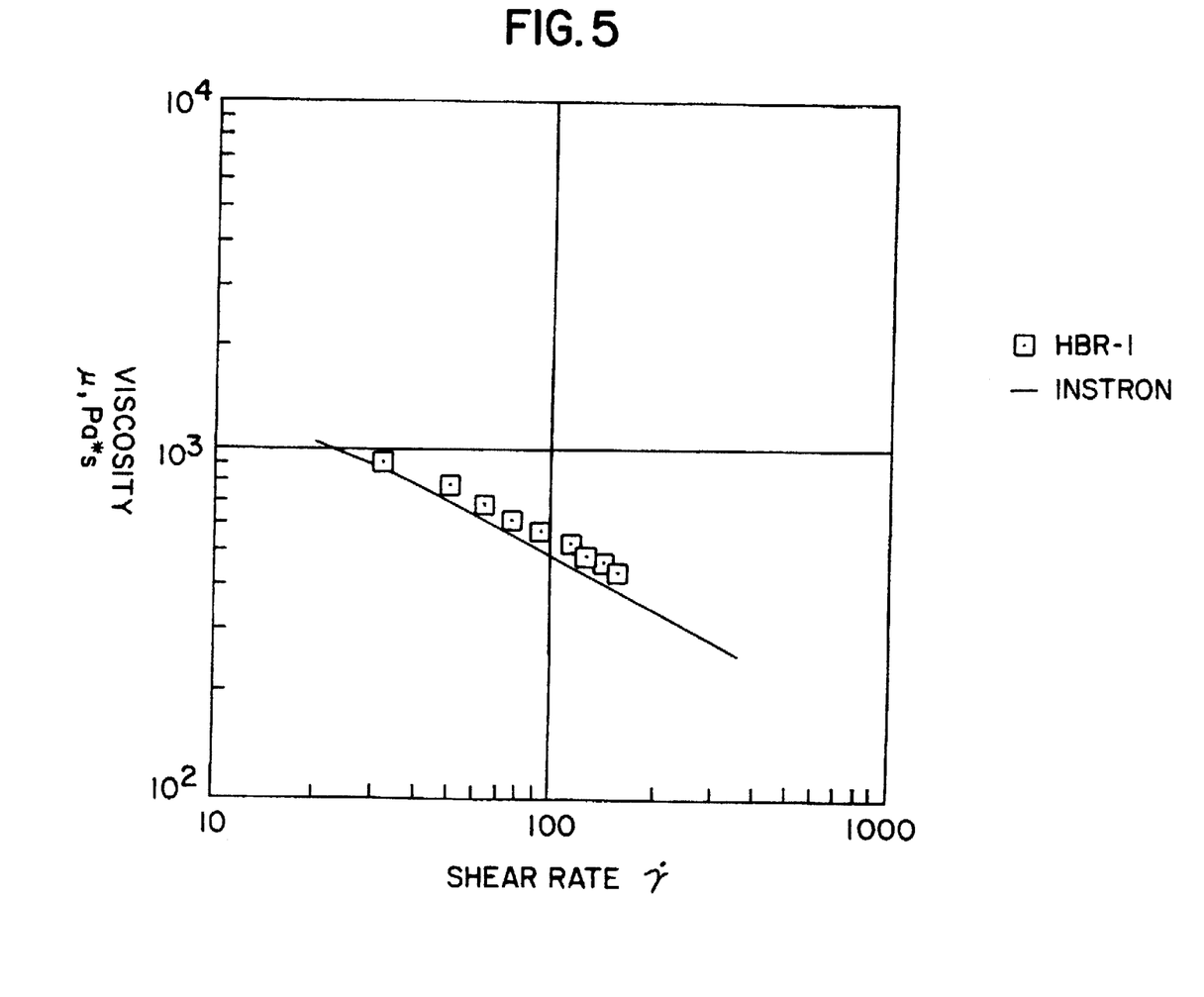
FIG. 5 shows experimental results of viscosity $\mu$ versus shear rate $\dot{\gamma}$ for the LDPE composition DOW 640 (2.0 MI) at 220° C. in both a first embodiment of the helical barrel rheometer of the invention and in an Instron Model 4204 capillary rheometer.
Figure 6:
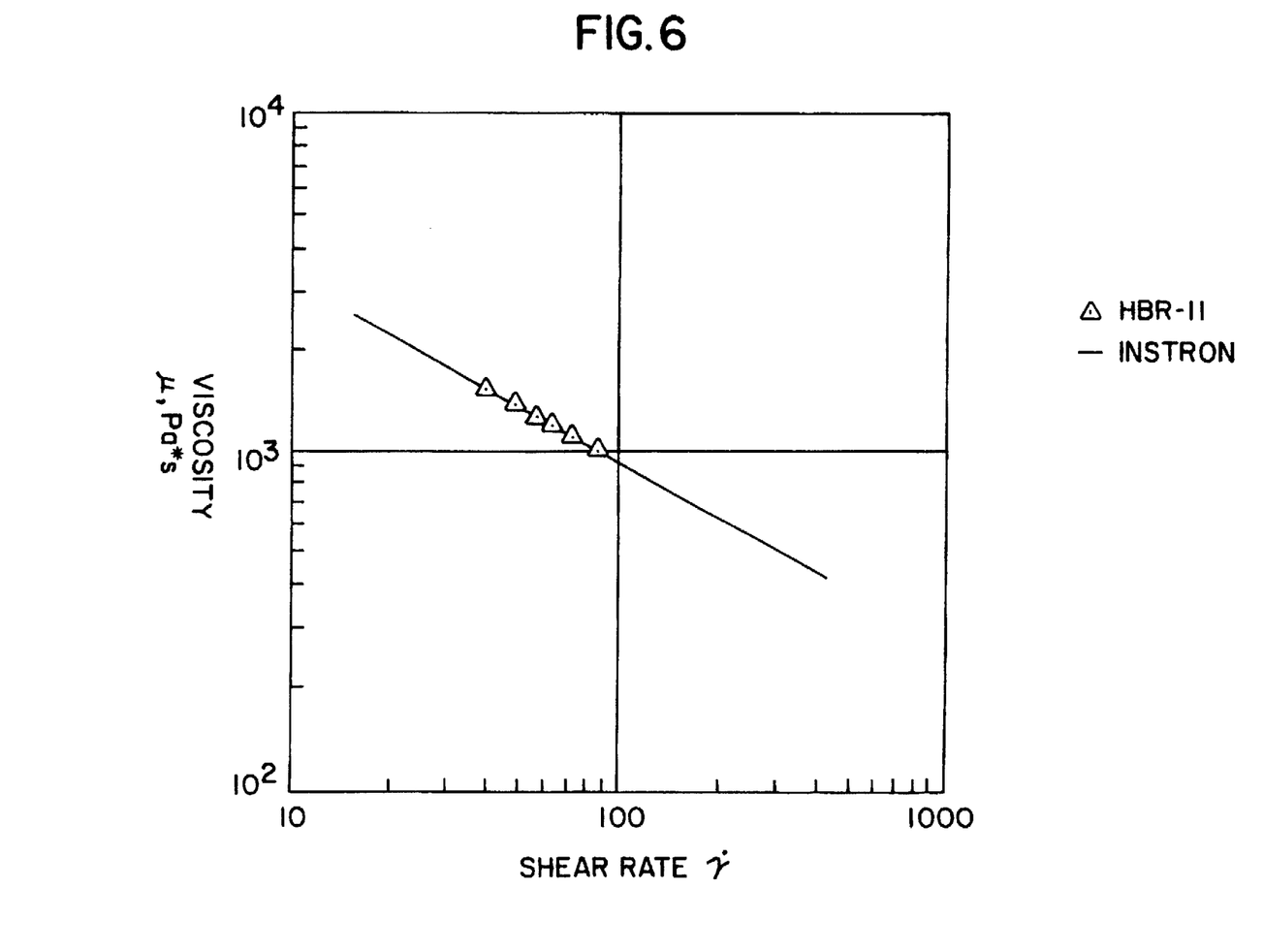
FIG. 6 shows experimental results of viscosity $\mu$ versus shear rate $\dot{\gamma}$ for the LDPE composition DOW 640 (2.0 MI) at 180° C. in both a second embodiment of the helical barrel rheometer of the invention and in an Instron Model 4204 capillary rheometer.
Figure 7:
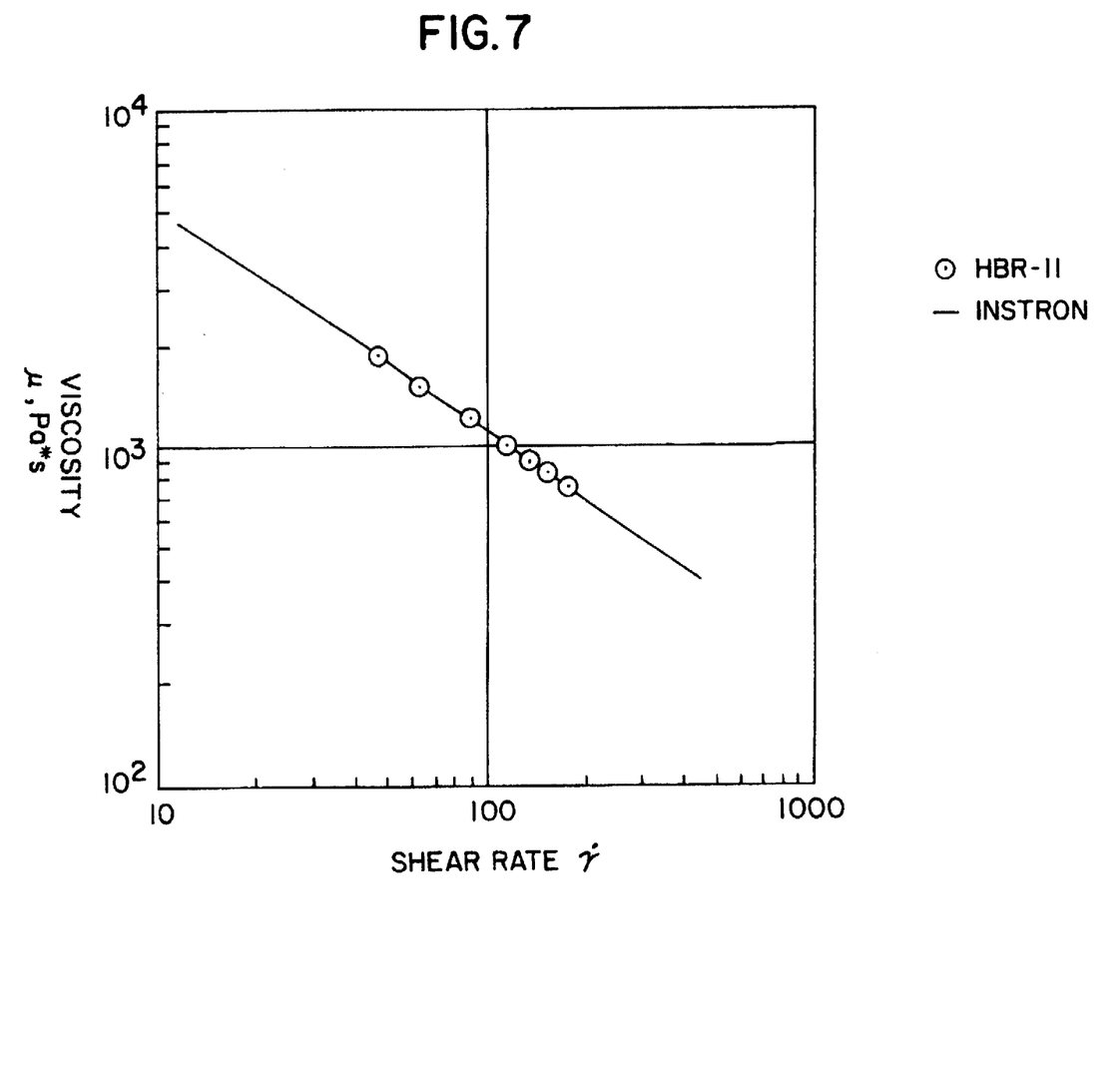
FIG. 7 shows experimental results of viscosity μ versus shear rate $\dot{\gamma}$ for the LDPE composition DOW 132 (0.22 MI) at 180° C. in both a second embodiment of the helical barrel rheometer of the invention and in an Instron Model 4204 capillary rheometer.

Typical data for the two rheometers tested are shown in FIGS. 5–7. FIG. 5 shows the viscosity $\mu$ versus shear rate $\gamma$ for the low density polyethylene (LDPE) DOW 640, 2.0 MI at 220° C. wherein "MI" represents "MFT" or melt index. The rheometer results are plotted alongside the straight line which represents viscosity measurements obtained from an Instron Model 4204 capillary rheometer. Similarly, data comparisons between Rheometer II and the Instron capillary rheometer for the same composition at 180° C. are presented in FIG. 6. FIG. 7 shows the data comparisons between Rheometer II and the Instron capillary rheometer for another LDPE composition having a lower melt index of 0.2, viz. DOW 132, at 180° C. As seen in FIGS. 5–7, the agreement between the viscosities measured by the helical barrel rheometers I and II and those measured by a typical capillary rheometer is excellent. Thus, the invention successfully addresses a long felt need in the measurements of viscosity to accurately and repeatably produce on-line measurements which are in agreement with laboratory measurements.

Thus, the invention makes possible the continuous monitoring of product from an extruder or reactor to assure quality and uniformity of that product.

The above examples are provided to illustrate some of the capabilities of the device, and are not intended to limit its scope.

It will thus be seen that the objects set forth above, among those elucidated in, or made apparent from, the preceding description, are efficiently attained and, since certain changes may be made in the above construction without departing from the scope of the invention, it is intended that all matter contained in the above description or shown on the accompanying drawing figures shall be interpreted as illustrative only and not in a limiting sense.

What is claimed is:

1. A rheometer for measuring at least one property of a composition comprising:
   a. a tubular housing member having an inner surface and an outer surface;
   b. a helical flange disposed on the inner surface of said housing member;
   c. a rotor disposed concentrically within said helical flange and abutting said helical flange while maintaining sliding contact with said flange, wherein said rotor and said helical flange define a helical channel therebetween, said helical channel having an entrance, an exit and at least one flight therebetween;
   d. means for rotating said rotor;
   e. means for introducing said composition into said entrance of said channel;
   f. means for controlling removal of said composition from said exit of said channel; and
   g. means for measuring a pressure difference of said composition in said helical channel between an upstream location and a downstream location, wherein said upstream location is disposed adjacent said helical chamber downstream of said entrance of said helical channel, and wherein said downstream location is disposed adjacent said helical chamber upstream of said exit of said helical channel in said channel.

2. The rheometer according to claim 1 further comprising means for measuring a temperature of said composition at a point between said entrance and said exit of said helical channel.

3. The rheometer according to claim 2 further comprising a means for controlling a temperature of said composition.

4. The rheometer according to claim 1 wherein said upstream location and said downstream location are situated at least one flight apart within said helical channel.

5. The rheometer according to claim 1 wherein said rheometer has the capability of allowing said composition to be continuously transported through said channel before and after measurement of said pressure difference.

6. The rheometer according to claim 1 wherein said tubular housing member is provided with at least one sensor tap extending generally radially therethrough and in communication with said helical channel.

7. A rheometer for measuring at least one rheological property of a composition comprising:
   a. a tubular housing member having an inner surface and an outer surface;
   b. a helical flange disposed on the inner surface of said housing member;
   c. a rotor disposed concentrically within said helical flange and abutting said helical flange while maintaining sliding contact with said flange, wherein said rotor and said helical flange define a helical channel therebetween, said helical channel having an entrance, an exit, and at least one flight therebetween;
   d. means for rotating said rotor;
   e. means for introducing said composition into said entrance o f said channel;
   f. means for removing said composition from said exit of said channel:
   g. means for measuring a pressure difference of said composition between an upstream location and a downstream location in said channel, situated at least one flight apart within said helical channel, wherein said upstream location is disposed downstream of said entrance of said helical channel, and wherein said downstream location is disposed upstream of said exit of said helical channel;
   h. means for measuring temperature of said composition at a point between said entrance and said exit of said helical channel; and
   i. means for controlling a temperature of said composition.

8. A rheometer according to claim 7 wherein said means for measuring a pressure difference in said helical channel includes a pressure transducer.

9. A rheometer according to claim 7 wherein said means for measuring temperature of said composition includes a temperature sensor.

10. A rheometer according to claim 7 wherein said means for introducing said composition into said helical channel further includes means for controlling the flow of said composition into said rheometer.

11. A rheometer according to claim 7 wherein said means for controlling removal of said composition further comprises a flow control valve and means for opening or closing said flow control valve.

12. The rheometer according to claim 7 wherein said housing member is provided with at least one sensor tap extending generally radially therethrough and in communication with said helical channel.

13. A method of measuring at least one rheological property of a composition comprising the following steps:
   a. placing said composition in contact with a rotating surface;
   b. dragging said composition in contact with said rotating surface along an enclosed helical path which is defined by said rotating surface and a stationary helical weir, thereby transporting said composition simultaneously in a rotational and an axial direction, whereby said composition is transported from an entrance to an exit of said helical path; and
   c. restraining the transport of said composition in the axial direction at said exit of said helical path while simultaneously measuring a pressure difference between an upstream and a downstream location in said helical path, wherein said upstream location is disposed downstream of said entrance of said helical path, and wherein said downstream location is disposed upstream of said exit of said helical path.

14. The method according to claim 13 further comprising the step of measuring a temperature of said composition in said enclosed helical path at a point between said entrance and said exit of said helical path.

* * * * *